(12) United States Patent
Cook et al.

(10) Patent No.: US 7,329,126 B2
(45) Date of Patent: Feb. 12, 2008

(54) USE OF BIOACTIVE GLASS

(75) Inventors: Richard J. Cook, London (GB); Timothy F. Watson, London (GB); Larry L. Hench, London (GB); Ian D. Thompson, London (GB)

(73) Assignees: King's College London Strand, London (GB); Imperial College Innovations Limited, London (GB)

( * ) Notice: Subject to any disclaimer, the term of this patent is extended or adjusted under 35 U.S.C. 154(b) by 72 days.

(21) Appl. No.: 10/109,011

(22) Filed: Mar. 29, 2002

(65) Prior Publication Data

US 2003/0008263 A1    Jan. 9, 2003

Related U.S. Application Data

(60) Provisional application No. 60/281,809, filed on Apr. 6, 2001.

(30) Foreign Application Priority Data

Mar. 30, 2001    (GB) ................................. 0108115.7

(51) Int. Cl.
*A61C 5/00*    (2006.01)
(52) U.S. Cl. ..................................... 433/215
(58) Field of Classification Search ................. 433/215, 433/216, 88, 87, 84
See application file for complete search history.

(56) References Cited

U.S. PATENT DOCUMENTS

| | | | |
|---|---|---|---|
| 4,579,530 A * | 4/1986 | McLaughlin | ................. 433/223 |
| 5,251,468 A | 10/1993 | Lin et al. | |
| 5,275,561 A * | 1/1994 | Goldsmith | ................... 433/216 |
| 5,573,446 A | 11/1996 | Dey et al. | |
| 5,634,956 A | 6/1997 | Suh et al. | |
| 5,735,942 A | 4/1998 | Litkowski et al. | |
| 5,865,620 A | 2/1999 | Kutsch | |
| 5,891,233 A | 4/1999 | Salonen et al. | |
| 5,934,287 A * | 8/1999 | Hayashi et al. | .............. 128/898 |
| 5,981,412 A | 11/1999 | Hench et al. | |
| 6,054,400 A | 4/2000 | Brink et al. | |
| 6,086,374 A | 7/2000 | Litkowski et al. | |
| 6,190,643 B1 | 2/2001 | Stoor et al. | |
| 6,244,871 B1 | 6/2001 | Litkowski et al. | |
| 6,338,751 B1 | 1/2002 | Litkowski et al. | |
| 6,342,207 B1 | 1/2002 | Stoor et al. | |
| 6,365,132 B1 | 4/2002 | Litkowski et al. | |
| 2002/0086039 A1 | 7/2002 | Lee et al. | |
| 2002/0098776 A1 | 7/2002 | Dopper et al. | |
| 2003/0008263 A1 | 1/2003 | Cook et al. | |
| 2004/0166172 A1 | 8/2004 | Rosati et al. | |

FOREIGN PATENT DOCUMENTS

| | | |
|---|---|---|
| EP | 0 832 619 A1 | 4/1998 |
| FR | 2543433 A1 | 10/1984 |
| WO | WO 96/10985 | 4/1996 |
| WO | WO 97/27148 | 7/1997 |
| WO | WO 99/13852 A1 | 3/1999 |

* cited by examiner

*Primary Examiner*—Melba Bumgarner
(74) *Attorney, Agent, or Firm*—Foley & Lardner LLP

(57) ABSTRACT

Bioactive glasses may be used as air abrasive agents in methods for treating or preventing dental hard tissue and pulpal disorders, such as dental pain.

27 Claims, 8 Drawing Sheets

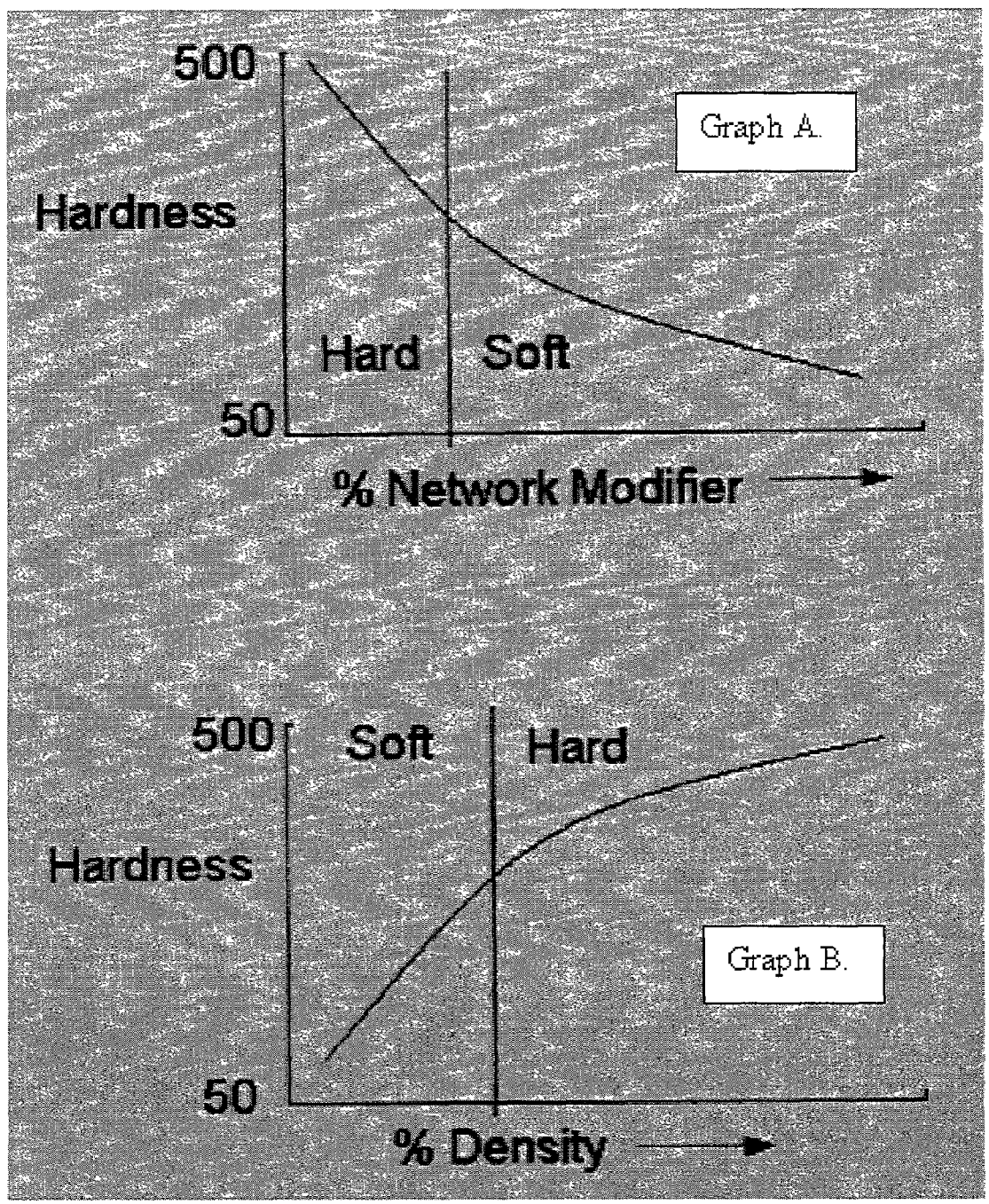
Fig. 8a - Graph A
Fig. 8b - Graph B

USE OF BIOACTIVE GLASS

The present invention relates to the use of bioactive glasses as abrasive agents in the management of dental pain.

Dental pain is a common problem affecting 17% of the population at any one time and increases in frequency with age. (Litkowski I J., Hack G D., Sheaffer H B., Greenspan D C., 1997, Occlusion of dentine tubules by 45S5 Bioglass®, Bioceramics 10 Procs $10^{th}$ Int., Symposium on ceramics in Medicine p411-414, Ed. Sedel L & Rey C. Elsevier Science Ltd.). The principle causes of this dental discomfort arise from both abrasion and acid erosion of external root dentine, which has either been revealed after gingival recession (due to periodontal disease or as a feature of maintaining teeth further into old age) or has developed due to dental caries i.e. the acid dissolution of dental tissues resulting from bacterial plaque metabolic activity.

One of the currently accepted causes of dental pain is the hydrodynamic theory (Litkowski, et al 1997) whereby movement of fluid through the dentine tubule tracts excites either the odontoblasts, whose processes (once) occupied the tubules, or adjacent nerve fibres directly. In the normal healthy state, these tubules are closed off by the overlying enamel crown or cementum of the root. When dentine is exposed either by the ravages of periodontal disease (gingival recession) or by dental treatment eg acid etching after cutting a restoration cavity, the tubules are lain open, allowing large fluid movements and consequential dental pain.

Regardless of its similarities, toothache resulting from cavity formation relates to a different problem area to hypersensitive dentine. Sensitivity associated with caries, and pain caused by irritation is usually treated by removal of decay and restoration by filling. At the bottom of the prepared cavity, a commercially available preparation is placed against the pulp, the biologically active component of such preparation is usually calcium hydroxide. At the cell level, the strongly alkaline calcium hydroxide first induces irritation, which leads to the necrotisation of the tissue. Over a longer time span, however, it promotes the healing process. The result of the treatment is the formation of reparative secondary dentine. The formed tissue layer separates the pulp from the damaged area or the filling, but its effect on the mineralisation of dentine tubules is minimal.

During filling, the dentinal tubules can also be closed by glass ionomer cement, or with different preparations based on polymer chemistry (binder plastics, resins, and dentine adhesives). These substances close dentinal tubules mechanically and improve the retention of the filling being prepared.

The epidemiological data describing the extent of the problem caused by hypersensitive dentine and the need for its treatment is limited. However, it is widely accepted that tubule occlusion by varnishes, resins or crystal precipitation will reduce or eliminate dentine sensitivity (Litkowski, et al 1997). The duration of the relief equates to the service lifetime of the occluding material (Litkowski, et al 1997), which can be all too brief e.g. if applied to a root surface continually abraded by a toothbrush.

Recently, in connection with tooth hypersensitivity, Litkowski, et al 1997 has shown in vitro that bioactive glasses can occlude exposed tubules and encourage re-mineralisation of the tooth surface.

U.S. Pat. No. 5,891,233 discloses preparations containing bioactive glass which act to induce mineralisation in exposed dentine and their use in the treatment of pulpal irritation i.e. tooth hypersensitivity and/or tooth strengthening. The bioactive glass demonstrated must be applied and maintained in moist form to encourage chemical interaction between the glass phase and the dentine.

Thus, in U.S. Pat. No. 5,891,233 the bioactive glass preparations are presented in the form of solutions, suspensions and pastes. In use, the bioactive glass preparation is placed in direct contact with the area of the tooth to be treated. For example, the paste or solution is placed in a periodontal pocket, in a drilled cavity or spread onto a polished surface or otherwise exposed dentinal surface. The bioactive preparation is then covered with protective packing or cementum to prevent displacement of the preparation.

However such methods suffer from the disadvantage that the area to be treated must first be prepared using conventional dental techniques. For example, in the case of cavity formation, the caries must first be removed with a drill or the like before the bioactive paste can be applied. Moreover, as mentioned above, when applied as a paste the bioactive preparation must be retained in place with protective packing for an extended period. In use such packing is prone to becoming detached and the paste then simply washes away. Moreover, when used to treat hypersensitivity the packing is often visible during the period of treatment. Such unsightly packing can lead to premature removal of the packing by the patient and thus failure of the treatment.

U.S. Pat. No. 5,735,942 discloses a novel silica based bioactive glass composition having a particle size range <90 μm for use in conjunction with a delivery agent such as a toothpaste, and the use of such compositions in treating dentine hypersensitivity.

U.S. Pat. No. 6,086,374 reports that the compositions of U.S. Pat. No. 5,735,942 may be used to remineralise enamel and prevent tooth decay.

Air abrasion as a means of cutting or preparing tooth substrate surfaces by harnessing the transferred kinetic energy of alumina particles accelerated in a controlled compressed gas stream has been known since the 1950s. The abrasive stream cuts (abrades) through the target substrate by repeated localised impacts serially removing material from the point of aim. More recently, dental "air polishing" employing bicarbonate of soda as an abrasive for tartar removal has gained acceptance.

The use of other gases as a propellant (eg $CO_2$ or $N_2$) is included in the definition of "air abrasion" and the use of water or other fluids to act as dust supression agents (regardless of potential contribution to the overall cutting effect) are also included, however delivered—either included in the gas stream or entrained around it (e.g. The Aquacut air abrasive machine—Medivance Instruments Ltd, Harlesden, London).

We have now found that by using bioactive glass as an abrasive agent (cutting and/or surface peening agent) in a conventional air abrasion system, benefits are observed in the cutting of both tooth enamel and dentine and in the delivery of the bioactive glass.

Accordingly the present invention provides a method of treatment for and/or prophylaxis of a person suffering from or susceptible to dental hard tissue and pulpal disorders, defined herein to include dental caries, pain, tooth wear, discolouration, dentine hypersensitivity and dental tissue congenital malformations, which method comprises contacting the affected area with bioactive glass using an air abrasion system.

Alternatively the present invention provides the use of a bioactive glass in the manufacture of an air abrasive agent for use in the treatment of dental disorders.

Thus the present invention is based upon the observation that when applied through a conventional air abrasion system the bioactive glass particles and fragments thereof become embedded in the surface of the treated area providing long term effect and minimising the amount of glass lost by erosion. The embedded bioactive glass provides long term effect, encouraging rapid re-mineralisation of the affected area, accelerating surface healing and reducing the patient's dental pain.

The fact that particles of bioactive glass are actually embedded in the surface of the treated area obviates the need for protective packing to prevent their displacement, thereby reducing the risk that the preparation will be washed away and increasing the success rate of the treatment.

Moreover, bioactive glass may be used as an abrasive agent in the air abrasive system to cut and abrade enamel and cariously damaged surfaces (i.e. de-mineralised enamel & dentine). Therefore the present invention obviates the need for a separate preparation step as required when using bioactive glass pastes and solutions to treat dental pain associated with caries.

Further advantages arise by carefully controlling the hardness and/or shape of the bioactive glass to be used, different types of dental material may be cut and/or abraded. Thereby giving rise to differential cutting and minimising the possibility of cutting too far.

BRIEF DESCRIPTION OF THE FIGURES

FIGS. 8a and 8b show the effect of network modifiers (hardening and softening agents) and density on glass hardness.

Figure 1:
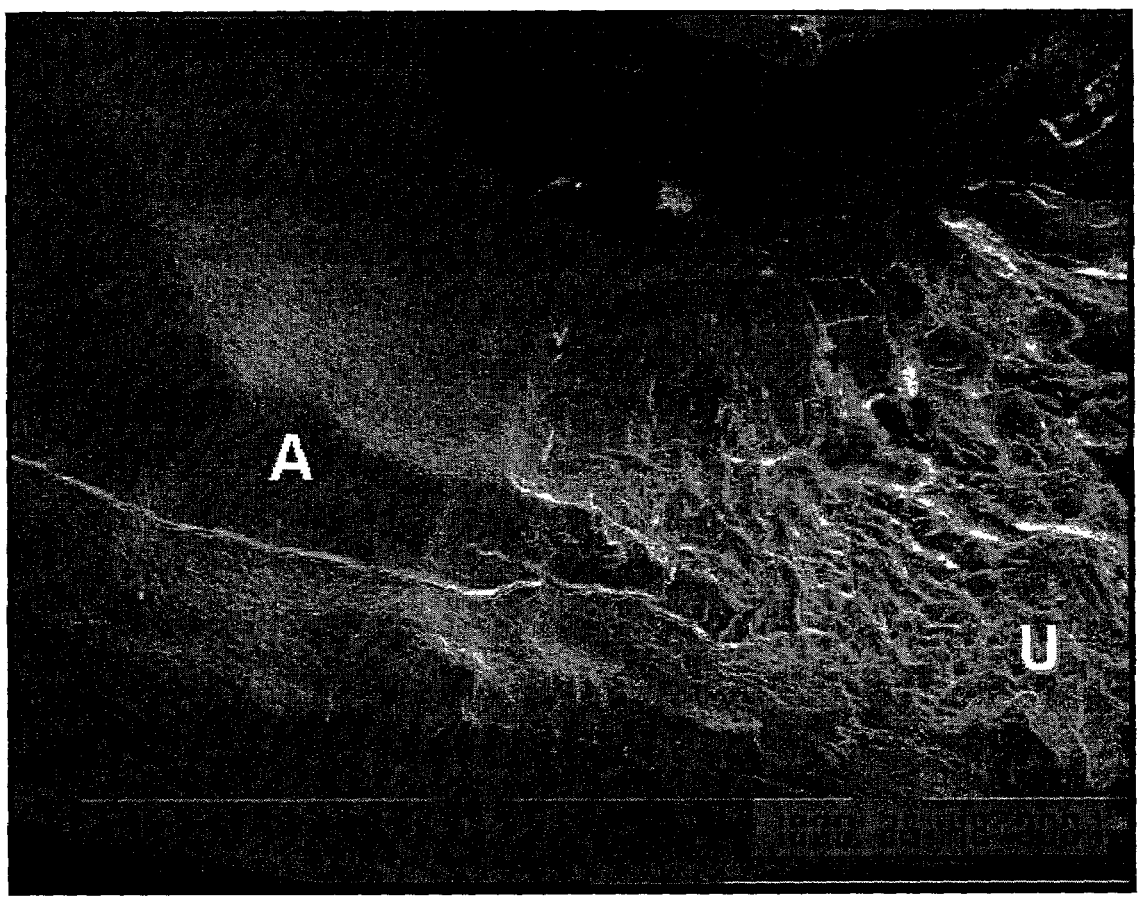
FIG. 1 compares untreated carious dentine (U) with carious root dentine that has been air abraded with 45S5 bioactive glass (A) viewed with a scanning electron microscope (SEM).

The term "bioactive glass" as used herein refers to a glass or ceramic material comprising Si-oxide or Si-hydroxide which is capable of developing a surface calcium phosphate/hydroxy-carbonate apatite layer in the presence of an aqueous medium, or at the interface of body tissues and the glass, so producing a biologically useful response.

Bioactive glasses suitable for use with the present invention include the silicon based bioactive glasses derived from the Sol-Gel process (Hench L L., West J K., 1990, The Sol-gel Process, Chem. Reviews, 90, 33-72) or the Melt process (Hench L L., Wilson J., 1993 Introduction to Bioceramics. Publisher: World Scientific).

Although it may be possible for a bioactive glass lacking a source of calcium or phosphorus to generate an apatite layer in vivo by utilising endogenous sources of these ions, typically a bioactive glass will comprise a source of at least one of calcium or phosphorous in addition to a source of Si-oxide or Si-hydroxide. Typically the bioactive glass will comprise a source of calcium. Optionally the bioactive glass may contain further hardening and/or softening agents. Such softening agents may be selected from: sodium, potassium, calcium, magnesium, boron, titanium, aluminum, nitrogen, phosphorous and fluoride. Additions of sodium, potassium, calcium and phosphorus are most commonly used, to reduce the melting temperature of the glass and to disrupt the Si networks within it. Optionally, hardening agents such as $TiO_2$ may be included in the glass composition. Its presence would allow crystallization to occur within its structure, so producing a glass—ceramic material, whose hardness will be greater than that of the glass alone. This will be of most benefit in producing a bioactive abrasive for cutting the harder dental structures e.g. enamel as discussed below.

Thus, composition ranges for bioactive glasses which may be used with the present invention are as follow:

| | |
|---|---|
| $SiO_2$ or $Si(OH)_2$ | 1-100% |
| CaO | 0-60% |
| $P_2O_5$ | 0-60% |
| $Na_2O$ | 0-45% |
| $K_2O$ | 0-45% |
| MgO | 0-40% |

Plus additions of Na, K, Ca, Mg, B, Ti, Al, P, N and F as necessary.

Preferably, a bioactive glass will contain between 30 and 100% Si-oxide or Si-hydroxide, more preferably between 40 and 85%.

In a further preferred embodiment the bioactive glass will contain between 5 and 60% Ca, more preferably between 30 and 55%.

With respect to a source of phosphorus, the bioactive glass will contain between 5 and 40% P, more preferably between 10 and 30%.

Thus, in one embodiment the bioactive glass will comprise $SiO_2$, CaO and $P_2O_5$. Preferably the bioactive glass includes from 44 to 86 weight % $SiO_2$, from 4 to 46 weight % CaO and from 3 to 15 weight % $P_2O_5$. Preferably the bioactive glass is prepared by the sol gel route and comprises from 55 to 86 weight % $SiO_2$, from 4 to 33 weight % CaO and from 3 to 15 weight % $P_2O_5$. Preferably such a bioactive glass has the composition 58 weight % $SiO_2$, 33 weight % CaO and 9 weight % $P_2O_3$.

In an alternative embodiment the bioactive glass composition may be prepared by the Melt method such as that described in U.S. Pat. No. 5,981,412. Such a glass may have a composition of from 40 to 51 weight % $SiO_2$, 23 to 25 weight % CaO, 23 to 25 weight % $Na_2O$ and 0 to 6 weight % $P_2O_5$. Preferably such a bioactive glass has the composition (by weight);

SiO2—45%
NaO2—24.5%

CaO—24.5%
P2O5—6%.

Such a bioactive glass is available commercially as Bioglass® 45S5.

The manufacturing and processing methods used in the silicon based bioactive glass family are ideally suited to the production of tailored particles for cutting under differing clinical conditions in restorative dentistry.

As mentioned above, hardening and softening components may be added to modulate the hardness of the bioactive glass and hence control the nature of the substrate it is able to cut. Typically, alumina particles are used in air abrasion systems. As can be seen from Table 1 alumina has a Vickers Hardness of 2300, harder than both tooth enamel and dentine. Thus when using alumina as the cutting agent the operator must carefully control the extent of cutting so as not to damage the tooth. A bioactive glass having a Vickers Hardness greater than that of enamel will cut through enamel and a bioactive glass having a Vickers Hardness intermediate between enamel and dentine will cut through the latter only. Thus, either by selecting from known bioactive glasses or by varying the amounts of hardening agents the skilled man will be able to prepare bioactive glass air abrasive agents capable of cutting through tooth enamel or dentine or both as necessary.

TABLE 1

|  | Vicker's Hardness Numbers. |
|---|---|
| Alumina | 2000-2300 |
| Glass beads | 500-550 |
| Crushed glass powder | 500-550 |
| Polycarbonate resin | 40-50 |
| Demineralised dentine model | not recordable |
| Enamel | 300 |
| Dentine (sound) | 70 |
| Bioglass ® 45S5 | 458+/−9.4 |
| Appatite/Wollastonite bioactive glass | 680 |
| 58S Sol-gel bioactive glass (fully densified) | 110 |

Cutting through enamel to gain access to decayed tooth substance ideally requires a hard bioactive glass such as Appatite/Woolastonite glass-ceramics or the hard angular particles of crushed 45S5 bioglass®. However, for selective removal of softened decayed dentine or the treatment of exposed sensitive dentine surfaces a weaker and more rounded particle is desirable. By controlling the processing conditions in the densification phase of the sol gel process (Hench L L., West J K., 1990, The Sol-gel Process, Chem. Reviews, 90, 33-72. Hench L L., West J K., 1996, Biological applications of Bioactive glasses, Life Chemistry Reports, 13, 187-241.) sol-gel variants of bioactive glass can be processed to differing densities and ultimate strengths and hardnesses to match resection or surface treatment needs. As shown in Table 1, a well densified 58S sol-gel Bioglass specimen yielded a Vickers Hardness of approximately 110 (less densified specimens have lower hardnesses) compared with alumina 2,300, sound human enamel 300, sound human dentine 70, whereas decayed dentine is too soft to record. Thus, for selective removal of decayed dentine from a cavity, or for sclerosing or obliterating dentine tubules on an exposed external sensitive dentine surface, to reduce or eliminate dentine sensitivity or pulpal pain, while minimising the damage to sound dentine, sol-gel bioglasses have the most promising physical characteristics.

Thus, by increasing the quantity of network modifier (non-silica species species, eg Na, K, Ca, Mn, Br, Al, N, P, Fl etc) the hardness of the finished glass decreases. (see FIG. 8a). These modifiers may be added to the melt derived glasses while in their molten states, or to sol-gel materials at the mixing phase of production. Hardness may also be decreased by increasing the porosity within the glass, achieved by variations in the drying and stabilisation and densification phases of the sol-gel process. As described above, the hardness of glasses can be increased by allowing crystal formation within them, so the use of TiO2 can act as a hardening agent, as the glass becomes a glass ceramic. Also modifications to the sol-gel processing phases allowing a more dense glass product will result in a harder product (see FIG. 8b).

A further consideration when preparing a bioactive glass for use in the present invention is the shape of the bioactive glass particles. These may be selected depending on the intended clinical application. Angular particles are better suited to cutting through hard materials such as enamel whereas rounded particles are more suited to the removal of soft tissue such as decayed dentine or sclerosing tubules on an exposed sensitive dentine surface. The shape of bioactive glass particles may be controlled by selecting the appropriate particulation process from, for example, grinding, crushing or air-collision milling during their manufacture. Thus, crushing produces sharper angulated particles, whereas, air collision milling will produce more rounded particles. Grinding (e.g. ball milling) however, will produce particles of a more intermediate shape. These processes being suitable for glasses produced by both the sol-gel and melt routes.

Particles most suitable for use in the present invention will have a diameter in the range of 1 μm to 1 mm, more preferably in the range of 10 μm to 500 μm.

Thus in treating a cavity one or more glasses may be employed to cut through the tooth enamel and/or dentine as required. Conventional air abrasion systems such as the Velopex® Alycat marketed by Medivance Instruments Ltd. permit switching the source of the abrasive agent. For cutting enamel the bioactive glass will preferably have a Vickers Hardness of at least 300 and the particle shape will preferably be angular. For selectively cutting dentine the glass will preferably have a Vickers Hardness of between about 70 and about 300 and the particle shape will preferably be more rounded. For selective removal of decayed dentine from a cavity, or for sclerosing or obliterating dentine tubules on an exposed external sensitive dentine surface the glass will preferably have a Vickers Hardness of between about 35 and about 150 and the particle shape will preferably be rounded.

It is to be understood that the present invention covers all combinations of suitable and preferred groups described hereinabove.

The present invention will now be illustrated, but is not intended to be limited, by means of the following examples.

EXAMPLE 1

To assess whether 45S5 bioactive glass will cut into and allow resection of carious dentine when used as an abrasive powder in an air abrasion system.

Method

Five freshly extracted, retained human roots were collected from two consenting patients, according to the local Hospital Ethical Committee Guidelines. The criteria for acceptance were, that the roots should be intact after removal and have been diagnosed as having active ongoing carious destruction across the entire root face, at the time of treatment.

The teeth were washed in normal saline and transferred directly to the lab in moist conditions using sealed glass specimen containers. With the minimum of delay (so avoiding desiccation artefacts) the apical dental fragments were mounted on a solid metal baseplate, using a low temperature thermoplastic "Dental Impression Compound" medium (Kerr Italia S.p.a, Salerno, Italy), with the carious root face uppermost.

Using a stainless steel traditional razor blade as a shield, an estimated 50% of each carious root face was protected, while the exposed area was subjected to air abrasive cutting. 20-90 μm diameter 45S5 bioactive glass particles were used as the abrasive, delivered through a modern commercially available "twin chambered" air abrasion machine (Medivance Instruments Ltd, London, England.). The abrasive was delivered through a 0.6 mm internal diameter nozzle at a constant 5 mm distance from the target, over a 5 second period, using an acceleration pressure of 0.5 MPa and a medium abrasive powder flow rate (0.01 g per second). All air abrasion activities were conducted within a purpose built self-evacuating chamber, to minimise environmental pollution (Handler, Westfield, N.J., USA). The five treated root faces were desiccated using a conventional silica gel vacuum chamber set up, prior to carbon coating and scanning electron microscopic (SEM) examination.

Results

FIG. 1 shows a representative image of the findings, clearly showing the cutting action that 45S5 bioactive glass has on carious root dentine, leading to removal of surface tissue, accompanied by smoothing & rounding of the treated surface, compared with untreated carious dentine. Despite the short exposure time, significant decayed tissue was removed and the residual dentine surface showed characteristics of an air abraded surface.

The results clearly showed that 45S5 bioactive glass could remove softened decayed dentine from a root surface when used as an air abrasive.

EXAMPLE 2

To establish whether the melt derived bioactive glasses would cut sound enamel and dentine and to examine any influence of the differential hardness of the two substrates on the overall rate of substrate removal. Furthermore, to establish whether bioactive glass particles and fragments thereof were present on the residual cut surface and whether dentine tubule orifices were closed or left patent at the surface after treatment.

Method

Five freshly extracted, human wisdom teeth were collected from four consenting patients, according to the local Ethical Committee Guidelines. The criteria for acceptance were, that the teeth should be intact after removal and have no clinical evidence of carious destruction or developmental anomaly, at the time of surgical treatment.

The teeth were washed in normal saline and transferred directly to the lab in moist conditions using sealed glass specimen containers. With the minimum of delay, (so avoiding desiccation artefacts) the teeth had their pulp tissue removed and were sectioned axially, using a water-cooled rotary diamond saw (Labcut 1010, Agar Scientific, Stanstead, Essex UK). The cut faces were then polished by hand to P1200 grit and acid etched in 37% phosphoric acid for 40 seconds (previously shown to remove all traces of a significant surface contaminant of silicon from the polishing process—identified in the SEM (Scanning Electron Microscope) using EDXA (Energy Dispersive X-Ray Analysis). The five hemisected teeth thus yielded 10 specimens, which were serially mounted with their sectioned surfaces uppermost and horizontal, on a solid metal baseplate, using a low temperature thermoplastic "Dental Impression Compound" medium (Kerr Italia S.p.a, Salerno, Italy).

The prepared enamel/dentine slices were evenly subjected to air abrasive cutting/peening for a total of 30 seconds, during which time, the operator was required to treat the entire sectioned surface of the tooth evenly. 20-90 μm diameter 45S5 bioactive glass particles were used as the abrasive, delivered through a modern commercially available "twin chambered" air abrasion machine (Medivance Instruments Ltd, London, England). The abrasive was delivered through a 0.6 mm internal diameter nozzle at a constant 5 mm distance from the target, using an acceleration pressure of 0.5 MPa and a medium abrasive powder flow rate (0.01 g per second). All air abrasion activities were conducted within a purpose built self-evacuating chamber, to minimise environmental pollution (Handler, Westfield, N.J., USA). The ten treated root faces were desiccated using a conventional silica gel lab vacuum chamber set up, prior to carbon coating and SEM examination.

Results

Figure 2:
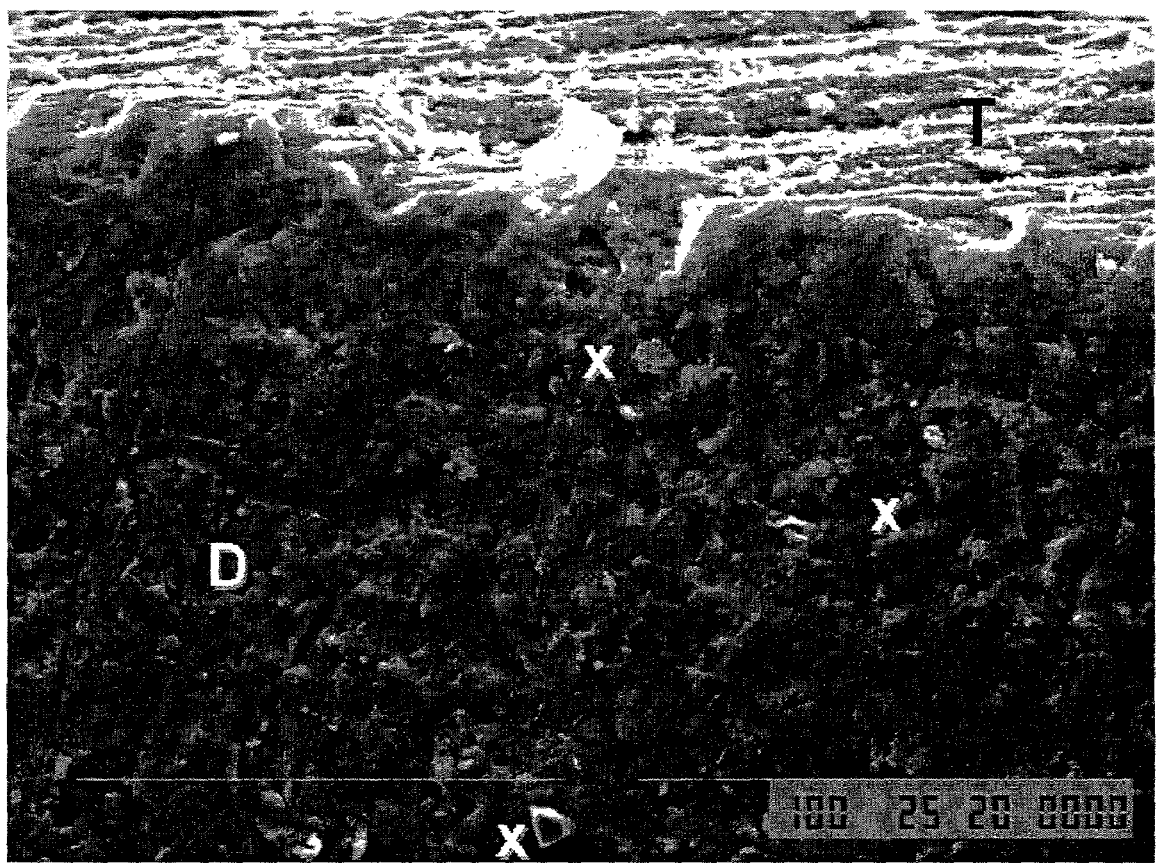
FIG. 2 shows the enamel (E)—dentine (D) junction (EDJ) of a prepared dental surface that has been air abraded with 45S5 bioactive glass particles viewed with a SEM.

Five of the treated specimens were examined whole in the SEM (FIG. 2), and all showed a similar scalloped residual cut surface pattern over both the enamel and dentine. Each showed a marked step height (20-30 μm) at the position of the Enamel-Dentine junction, the naturally softer dentine element having been removed to a greater extent than the harder enamel.

On examining the enamel surface structure itself, further evidence of differential cutting was identified, as the Hunter-Schreger bands (a well recognised, normal anatomical structure) were readily identifiable, themselves being somewhat more resilient to air abrasive cutting (Boyde 1984).

Figure 3:
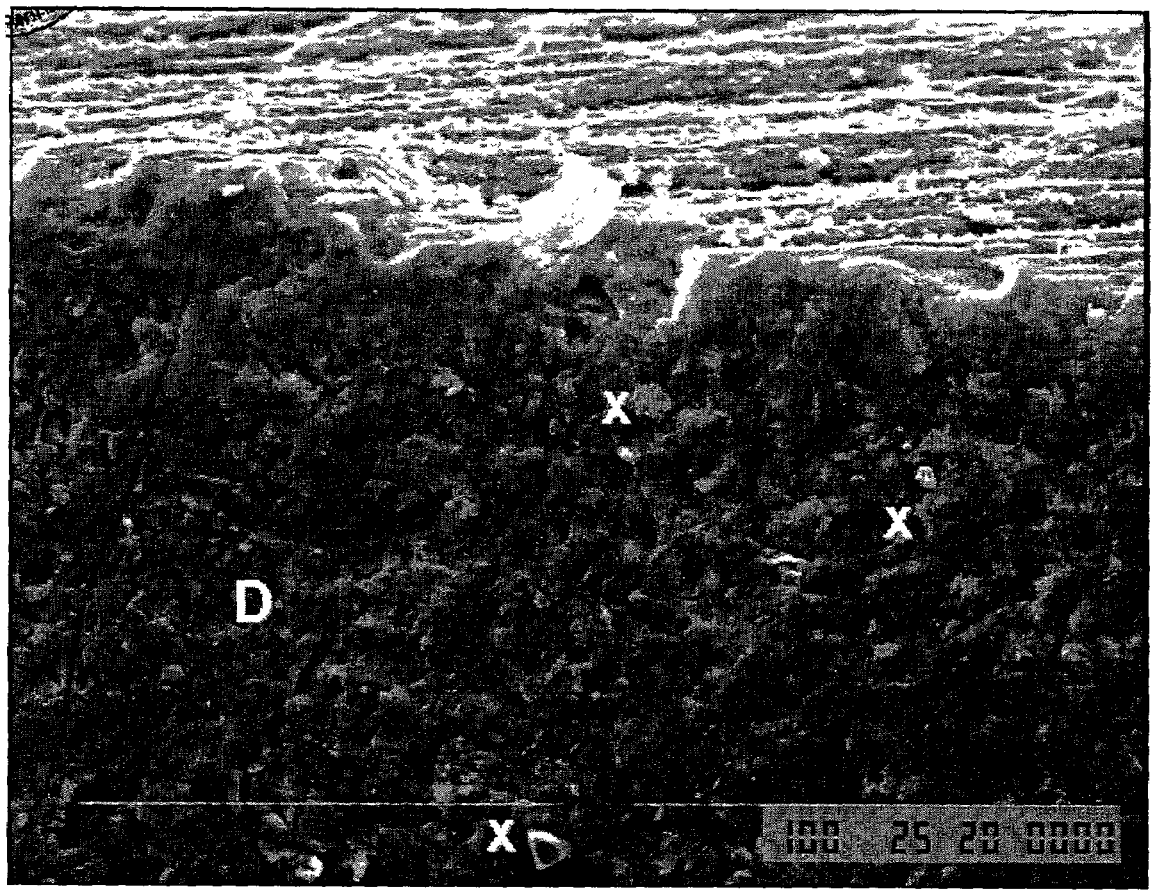
FIG. 3 illustrates SEM examination of the dental surface shown in FIG. 2 having been cleaved along an axis perpendicular to that of the treated surface (D).

The remaining five specimens were cleaved using a Dental surgeon's osteotome and mallet, first lodging the tooth firmly in the corner of a piece of heavy angle iron. The impact was targeted at the lowermost extremity of the tooth with the intention of cleaving the hemisected specimen axially, so revealing the untreated dentine tubule structure in a plane perpendicular to the exposed surface. FIG. 3 clearly shows dentine tubules coursing towards the treated surface, but none ends in an open orifice as one would expect to see if a phosphoric acid etched dentine surface was similarly examined.

Furthermore, the cut/peened dentine surface illustrated in FIG. 3 clearly showed evidence of residual particles on and embedded in the treated surface. (It should be remembered that these particles had withstood the high energy cleaving impact, prior to SEM scanning.) EDXA analysis of these particles revealed a clear silicon signal, indicating it was debris from bioactive glass, as the polishing silicon adulteration was removed by the acid etch process described. This was further confirmed by EDXA traces taken of material between the particles failing to register the presence of significant silicon peaks.

That the differential cutting was identifiable within one structure as well as between two different elements of the tooth indicates that the hardness of the substrate will influence the rate at which it is cut by bioactive glasses. Thus, by matching the hardness of a bioactive glass to that of softened dentine will allow selective removal of diseased dentine. Furthermore, materials matched to the hardness of intact dentine should peen or minimally cut the sensitive surface, while occluding its tubules, providing long-term pain relief. Such a material should have a negligible effect on the far harder surface enamel, while removing adherent tartar and unsightly staining deposits, thus capitalising on the differential cutting phenomenon.

The clear demonstration of residual bioactive glass particles and fragments (far smaller than the original abrasive employed, indicating a shattering of the abrasive on impact) resiliently sited on/in the treated surface provides the vehicle for the desired bioactive response of generation of a new calcium phosphate surface over the exposed treated surfaces. By definition, the bioactive glasses all generate a calcium phosphate surface, overlying an ion depleted silica gel layer. This new physic-chemically created mineral surface (generated without cellular assistance or control) will allow the re-mineralisation and repair of decayed tooth structures at the finished cavity surface—i.e. the limit of caries disease resection within a tooth, or allow a treated, sensitive exposed dentine surface to acquire a more resilient and long lasting desensitised mineralised surface. The hydration source will be either super-saturated (Ca—P) solution of saliva, or the tissue fluid naturally found within the tubules of dentine, so rendering it a "wet" material in vivo. Both fluids are well recognised as abundant Ca and P sources.

EXAMPLE 3

To establish whether the cut/peened surface created by the bioactive glasses and having a deposition of bioactive particles and fragments thereof on the surface would withstand the rigours of an intra oral existence and to identify any possible evidence of new calcium phosphate deposits accreting on the cut surface.

Methods

Figure 4:
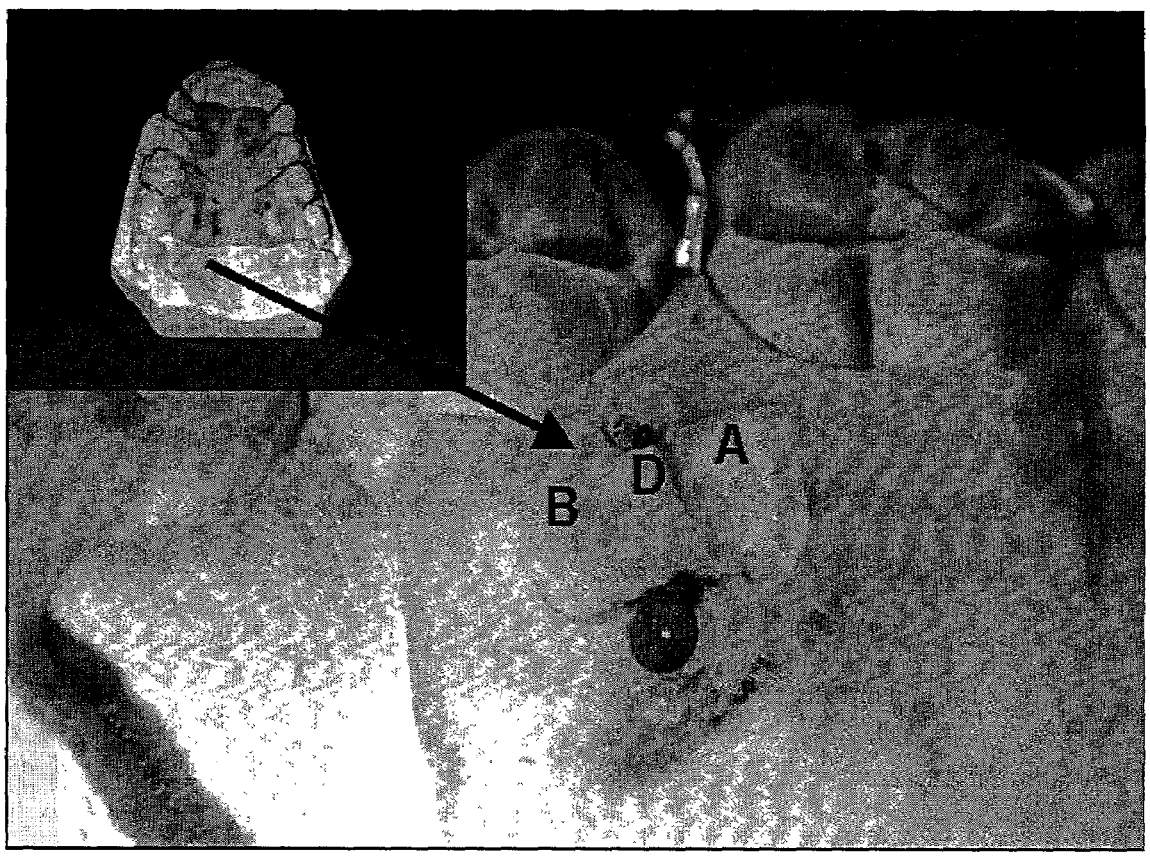
FIG. 4 illustrates a section of human dentine, mounted in an orthodontic retainer style baseplate. The Figure compares bioactive glass treated surface (B) and alumina treated area (A). Intervening dentine bridge (D) provides a negative control for the surfaces.

Four volunteers agreed to have an intra-oral prosthesis made, along the lines of a crib retained orthodontic appliance (inactive)—FIG. 4. Each appliance bore four specimens of enamel and dentine that had been previously rendered sterile against bacterial, viral and prion transfer, using two cycles of SDS detergent treatment (5% solution of Sodium dodecyl sulphate for 24 hrs) (Azzopardi 2000: Measurement of erosion and protecting exposed dentine with an adhesive resin coating:—an in vitro and in situ evaluation. PhD Thesis of GKT Dental Institute—Guy's Campus, King's College, University of London) and gamma irradiation (600 curies at 22,272 Rad/hr Caesium 137 source Gammacell 1000 Elite Nordion Int. Inc. Ontario). A single 24 hour dose of Gamma radiation was used as it proved safest in a pilot investigation to test the method of sterilisation (Azzopardi 2000).

Following the local Hospital Ethical Committee protocols, each of the dental test specimens were cut from a pair of undamaged extracted human third molars (which had previously had the pulp tissue removed), using a water cooled rotary diamond saw (Labcut 1010, Agar Scientific, Stanstead, Essex UK). The slabs (16 in total) were polished to P1200 grit and mounted in the acrylic baseplate using a cold cure orthodontic PMMA resin (Ortho-resin). The specimens were subsequently exposed to 37% phosphoric acid for 40 seconds to clean off their adulterated surface and to reveal the truly porous dentine structure (see example 2). The central portion of each specimen was then protected using a 3 mm wide strip of PTFE tape, to avoid any contamination of this control site.

Using a stainless steel traditional razor blade as a shield, the anterior portion of each specimen only, was subjected to air abrasive cutting. 20-90 µm diameter 45S5 bioactive glass particles were used as the abrasive, delivered through a modern commercially available "twin chambered" air abrasion machine (Medivance Instruments Ltd, London, England.). The abrasive was delivered through a 0.6 mm internal diameter nozzle at a constant 5 mm distance from the target, over a 5 second period, using an acceleration pressure of 0.5 MPa and a medium abrasive powder flow rate (0.01 g per second). By reversing the razor blade shield again, the anterior ⅔ portion of each specimen was then protected while the posterior portion underwent air abrasion with comparable diameter alumina particles. All air abrasion activities were conducted within a purpose built self evacuating chamber, to minimise environmental pollution (Handler, Westfield, N.J., USA).

The air abrader instrument settings remained unchanged throughout the experiment, although the lines were cleared of residual bioactive powder by allowing a 2 minute period of waste spraying into the "dust chamber." The specimens were blown clean, using dry compressed air and the protective tape was removed. The appliances were kept moist in orthodontic retainer boxes while awaiting periods of wear.

Following a well accepted daily wear protocol (Azzopardi 2000) the appliances were worn for eight hours per working day by all volunteers, but were removed at mealtimes in an attempt to allow hygienic handling of the specimens at reviews (pre wear, at 3 days and 1 week). Each review, comprised examination of all three areas of each dentine/enamel specimen with a tandem scanning confocal reflected light microscope (Noran Instruments Middlenton, Wis., USA) using a ×40/0.55 na dry lens (Nikon Corp. Japan), so avoiding any surface contamination with microscopist's lens oil. Digital images of representative portions of each surface were captured using an eyepiece mounted Coolpix 990 Digital Camera (Nikon Corp. Japan). The mounted specimens could not be repeatedly examined in the SEM and Direct reflection imaging was preferred to resin copying techniques as this avoided any further disruption to the surface than was required.

Results

Figure 5:
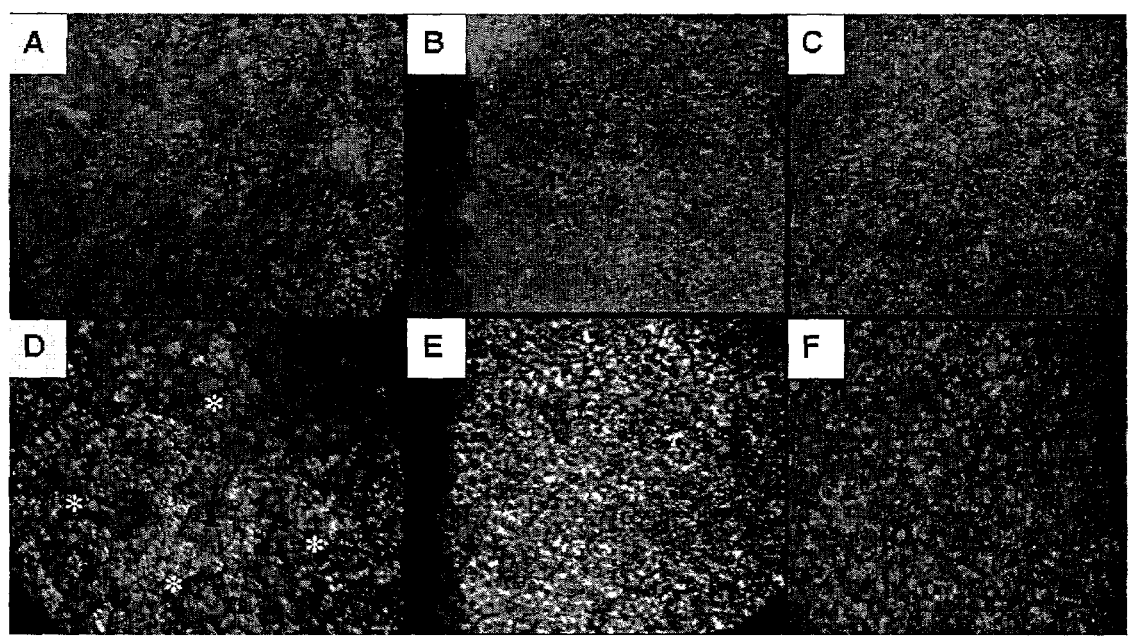
FIG. 5 shows comparable Tandem Scanning Confocal surface reflection images at ×400 magnification of the experimental dentine surfaces. (A), (B) and (D) in—FIG. 4—taken over a full week wear period. Images A and D of FIG. 5 illustrate area (B—FIG. 4) at the beginning and end of the trial period respectively. Images B and E of FIG. 5 illustrate area (D—FIG. 4) at the beginning and end of the trial period respectively. Images C and F of FIG. 5 illustrate area (A of FIG. 4) at the beginning and end of the trial period respectively.

FIG. 5 shows a montage of the images retrieved from one representative specimen over the full week wear period. Images A and D correspond to area (B) of FIG. 4 at the beginning and end of the trial period, images B and E correspond to area (D) of FIG. 4 at the beginning and end of the trial period and images C and F correspond to area (A) of FIG. 4 at the beginning and end of the trial period. The first apparent feature is the alteration of the open tubule dentine pattern by air abrasion/peening with both alumina and bioactive glass particles. An optically similar pattern is achieved, with closure of the open tubule orifices. In FIG. 5, image D shows no degradation of the surface after a week's intra oral wear. The presence of blue on green in the image is an optical phenomenon: chromatic aberration, indicating a higher area of the surface, which suggests the development of a new surface feature (Watson 1997). The untouched dentine surface (E) showed a little similar change over the same period, yet the alumina treated surface (C-before & F-after the trial period) showed none. The lack of similar additional features on the alumina surfaces implies a resilient accretion or mineral growth phenomenon, accelerated on the dentine surfaces treated with bioactive glasses. If the phenomena was transient debris, it stood an equal chance of appearing on the other surfaces too, yet none was found in any of the specimens examined.

That similar new accretions were not seen on the alumina treated surfaces also fits with the suggestion that this new material is indeed a new calcium phosphate deposit, as in the presence of greater than 3% alumina, the bioactive reaction is known to be killed (Hench 1998).

By way of confirmation of the previous results, it was noted that without exposing the teeth to the desiccation necessary for SEM preparation, the classical step height was maintained in the bioactive glass sprayed EDJ regions, indicating that the dentine was truly removed at a faster rate than the harder enamel. The alumina sprayed surface showed a more rapid removal of tissue (FIG. 4) and the EDJ step height was far less prominent as both substrates were so much softer than alumina particles.

The images shown clearly demonstrate the altered surface achieved using bioactive glasses as air abrasives. The maintenance of closure of the tubule orifices during intra oral wear suggests the surface is resilient and the altered morphology over time, further substantiates the claim that the bioactive glass abrasive debris is capable of seeding the generation of a calcium phosphate mineral surface, in the intra-oral in service environment, at a rate far faster than exposed dentine and that treated with alumina.

EXAMPLE 4

Corroborative demonstration of the differential cutting of similar sized particles of different hardness.

Methods

Two monolithic slabs 1 cm×1 cm×3 mm deep of 58S sol-gel bioactive glass were sawn into comb shapes using a diamond wire saw (Bennettech, Leicester, England). Each tyne of the comb was 2 mm wide and 6 mm long. Resting each comb on a bed of low temperature thermoplastic "Dental Impression Compound" medium (Kerr Italia S.p.a, Salerno, Italy), allowed the test substrate to be held in a horizontal position in the spraying chamber. Using stainless steel razor blades as protective shields between the tynes, each test surface could be air abraded without damaging or adulterating the neighbouring specimens. Each comb yielded three tynes, affording three each of two abrasive test sites.

Each specimen was subjected to air abrasive cutting, using either 20-90 μm diameter 45S5 bioactive glass particles or a similarly sized alumina particulate, delivered through a modern commercially available "twin chambered" air abrasion machine (Medivance Instruments Ltd, London, England.). The abrasive was delivered through a 0.6 mm internal diameter nozzle at a constant 5 mm distance from the target, over a 5 second period only, using an acceleration pressure of 0.5 MPa and a medium abrasive powder flow rate (0.01 g per second). All air abrasion activities were conducted within a purpose built self evacuating chamber, to minimise environmental pollution (Handler, Westfield, N.J., USA). The air abrader instrument settings remained unchanged throughout the experiment, although the lines were cleared of residual bioactive powder by allowing a 2 minute period of waste spraying into the "dust chamber." The specimens were blown clean, using dry compressed air and then transferred to the SEM facility for gold coating and imaging.

Results

Figure 6:
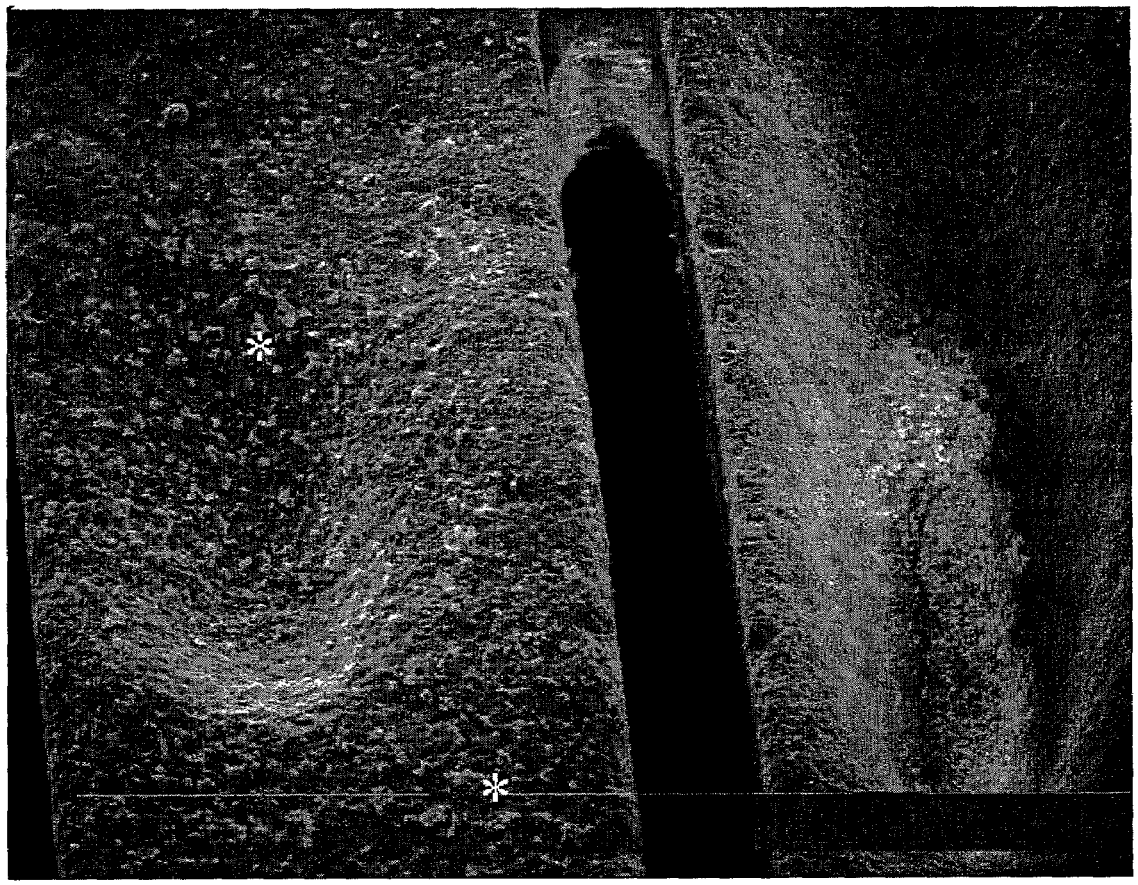
FIG. 6 shows two tynes of a 58S sol-gel bioactive glass comb one abraded with 45S5 bioactive glass and the other with alumina, viewed under SEM.

FIG. 6 is presented as representative of the findings. The surfaces treated with 45S5 bioactive glass were indented far less than those subjected to alumina treatment.

The 45S5 bioactive glass left residual particles of itself imbedded in/on the cut surface, whereas the harder grit produced a cleaner surface. (A plug of material seen impacted in the base of the alumina resection area was due to choking of the cutting apparatus.)

The data shown in FIG. 6 clearly demonstrates that abrasive aggregates of differing hardness will have very different cutting effects when applied to the same substrate under the same cutting conditions, so supporting the proposition of differing abrasive properties having differing cutting, finishing and minimally resecting surface treatment roles.

EXAMPLE 5

Demonstration of tubule closure after use of the invention in an in-vivo model.

Methods

The experiment established in Example 3 was allowed to continue for a period of 13 days in total, at the end of which, the specimens were retrieved from the base-plates by careful sectioning, ensuring there was no contamination of the exposed, treated dentine surfaces. Each specimen was clearly marked to allow accurate re-orientation. Following a well established practice for identifying the movement of dentine bonding agents through tooth tissue (Griffiths B M, Watson T F, Sherriff M,. 1999 The influence of dentine bonding systems and their handling characteristics on the morphology and micro-permeability of the dentine-adhesive interface. J. Dent. 27 63-71), an excess of Rhodamine-B labelled dentine bonding resin (EBS Bond Espe, Seefeld, Germany) was puddled over the horizontally orientated dentine test surfaces and allowed to soak into the tubules as best it could over a two hour period. The resin's polymerisation and set, was avoided by keeping the samples in total darkness for the experimental period. (Old photographic film containers served well as light proof chambers.) No sample showed premature set of the resin at the end of the soak phase. The Resin was conventionally command set at the end of the two hour period using the manufacturer's supplied 470 nm wavelength curing light.

Figure 7:
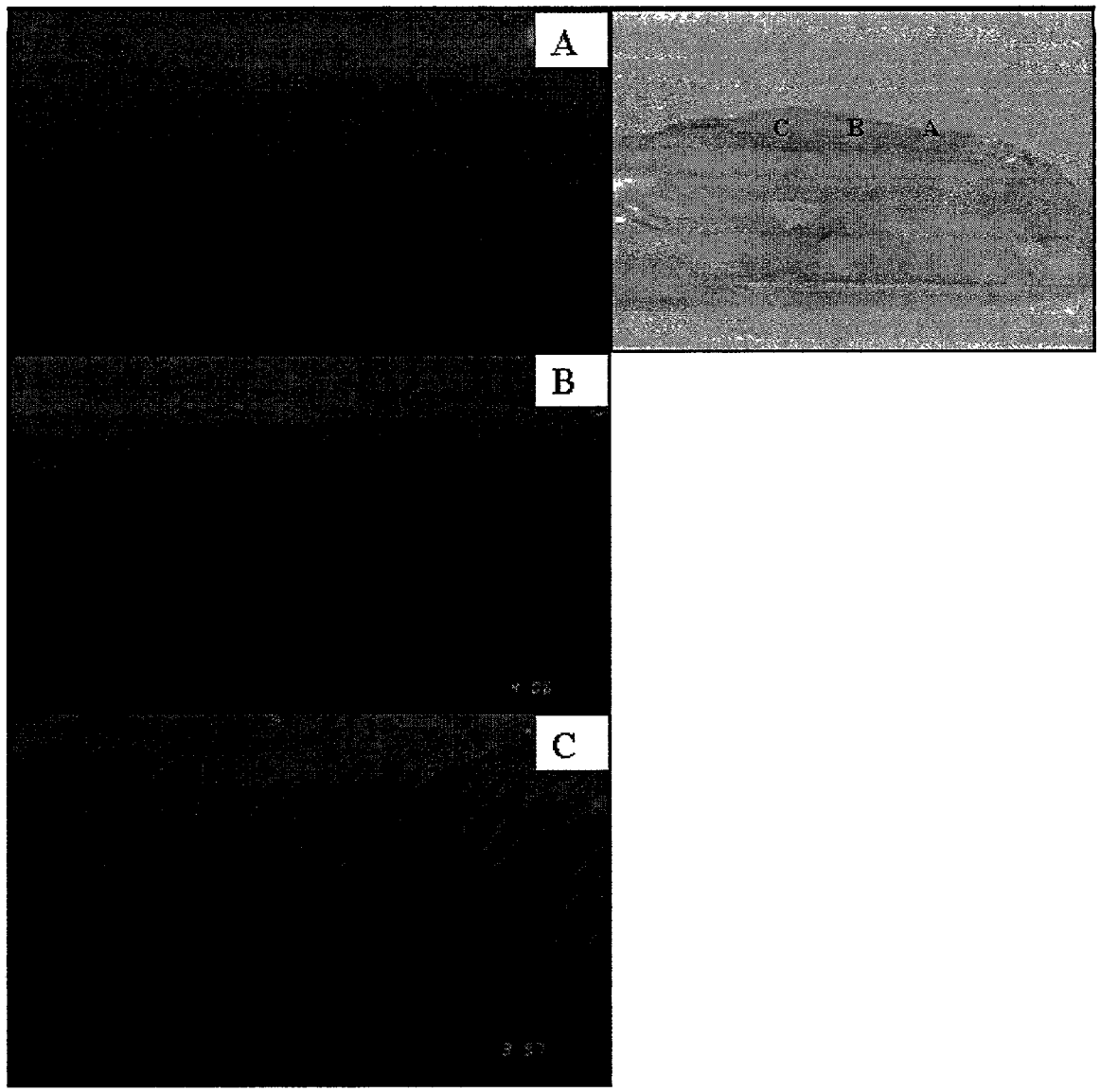
FIG. 7 shows tandem scanning confocal fluorescence microscopy images of the tooth specimens retrieved from the experiment in FIG. 5, having been sectioned.

Using a water-cooled rotary diamond saw (Labcut 1010, Agar Scientific, Stanstead, Essex UK), the specimens were sectioned to reveal any labelled resin penetration perpendicular to the experimental surface (see FIG. 7.) the cut faces were then polished by hand to P1200 grit, prior to viewing with a tandem scanning confocal fluorescence light microscope (Noran Instruments Middlenton, Wis., USA) using a ×60/1.40 na oil lens (Nikon Corp. Japan) and ×10 objective giving a magnification of ×600 for the images (FIG. 7.) The confocal microscope allowed sub surface imaging in such translucent specimens, so avoiding confounding by any smear layer from the cutting/polishing phase.

Results

FIG. 7. Composite image showing tandem scanning confocal fluorescence imaging of a representative dentine tooth slab, hemisected after 13 days intra oral wear. The specimen is shown, opposite Part A, the Bioactive glass treated area, and no labelled resin penetration is seen. Occasional shadow marks of empty tubules are seen, illuminated by the fluorescence signal from the surface resin. Note that no tubule markings are visible at the tooth-resin interface, indicating the development of a new sealing surface layer. Part B shows the response of exposed dentine to the same intra-oral environment. Some patent tubules remain, although most are sealed off within their lumens, indicating a different, slower, stenotic mechanism. Part C shows the alumina treated surface of the same specimen. Clearly, the tubules have not been closed and no additional remineralisation is able to occur, presumably because the bioactive response is being poisoned by the alumina debris. Thus it would seem that the currently available abrasive, while cutting rapidly (note excessive loss of tissue height in the alumina treated region -C of specimen view.) hinders all chance of any surface remineralisation, by whatever mechanism. Furthermore, the bioactive glasses accelerate the formation of a new mineralised surface, providing a seal faster than the untreated dentine surface.

Discussion

As is clearly seen from the images in FIG. 7, that over the experimental time period, the dentine was able to partially heal itself, as only few resin tags were present in the sectioned faces examined. This was an expected finding as it is known that dentine can slowly sclerose any open tubules by CaP crystal growth, when in a suitable environment. The dentine surfaces treated with bioactive glasses however, did not permit any access to any of the labelled resin, only the shadows of the empty closed off tubules could be seen, illuminated by the radiant light from the labelled resin on the dentine surface. The images also show that few if any tubules extend to the tooth—resin interface, implying a peripheral closure of the tubules by new mineral deposition, unlike the exposed dentine interface, where resin can be seen entering open tubule orifices. The sclerosis/stenosis process would seem to be occurring within the patent tubule, discriminating between this process and the surface healing phenomenon seen in the bioactive glass treated surfaces.

The dentine treated with alumina showed a remarkable degree of leakage, the image in FIG. 7, clearly showing labelled resin permeating throughout the tubule network in the imaged field. The presence of greater than 3% alumina in the vicinity of a bioactive process is known to kill the reaction completely. It would seem that this has occurred in this experiment, the treated surface being rendered incapable of further CaP salt crystallisation. This evidence confirms that the deposition of bioactive glasses on tooth surfaces cut or peened by this method, can allow accelerated mineral crystalisation on the treated areas, altering the surfaces in a beneficial way for use in the resection, arrest and treatment of dental caries, dentine hypersensitivity and pulpal pain, congenital dental hard tissue defects, discolouration and tooth wear.

The invention claimed is:

1. A method of treating a human suffering from or susceptible to a dental hard tissue or pulpal disorder, comprising applying a bioactive glass as an air abrasive agent directly to an area of the body of the human affected by or susceptible to the hard tissue or pulpal disorder.

2. A method according to claim 1, wherein the bioactive glass comprises a source of $SiO_2$ or $Si(OH)_2$, and a source of $CaO_2$ or $P_2O_5$.

3. A method according to claim 2, wherein the bioactive glass further comprises at least one hardening agent, at least one softening agent or a combination thereof.

4. A method according to claim 3, wherein the softening agent is selected from the group consisting of Na, K, Ca, Mg, B, Al, P, N, F and the hardening agent is $TiO_2$.

5. A method according to claim 1, wherein the bioactive glass comprises 1 to 100 weight % $SiO_2$ or $Si(OH)_2$, 0 to 60 weight % CaO, 0 to 60 weight % $P_2O_5$, 0 to 45 weight % $Na_2O$, 0 to 45 weight % $K_2O$ and 0 to 40 weight % MgO.

6. A method according to claim 1, wherein the bioactive glass is obtainable by the sol-gel method.

7. A method according to claim 6, wherein the bioactive glass comprises 44 to 86 weight % $SiO_2$, 4 to 46 weight % CaO and 3 to 15 weight % $P_2O_5$.

8. A method according to claim 6, wherein the bioactive glass comprises 58 weight % $SiO_2$, 33 weight % CaO and 9 weight % $P_2O_5$.

9. A method according to claim 1, wherein the bioactive glass is obtainable by the melt method.

10. A method according to claim 9, wherein the bioactive glass comprises 47 to 51 weight % $SiO_2$, 23 to 25 weight % CaO, 23 to 25 weight % $Na_2O$ and 0 to 6 weight % $P_2O_5$.

11. A method according to claim 9, wherein the bioactive glass comprises (by weight):
$SiO_2$—45%
$Na_2O$—24.5%
CaO—24.5%
$P_2O_5$—6%.

12. A method according to claim 1, wherein the bioactive glass has a Vickers Hardness of at least that of tooth enamel.

13. A method according to claim 12, wherein the bioactive glass has a Vickers Hardness of at least about 300.

14. A method according to claim 12, wherein the bioactive glass are substantially non-spherical.

15. A method according to claim 1, wherein the bioactive glass has a Vickers Hardness of at least that of healthy tooth dentine and at most of that of tooth enamel.

16. A method according to claim 15, wherein the bioactive glass has a Vickers Hardness of at least about 70 and at most about 300.

17. A method according to claim 15, wherein the bioactive glass are substantially spherical.

18. A method according to claim 1, wherein the bioactive glass have a diameter of from 10 μm to 500 μm.

19. A method according to claim 1, wherein the bioactive glass is capable of cutting through tooth enamel.

20. A method according to claim 1, wherein the bioactive glass is capable of cutting through tooth dentine and not tooth enamel.

21. A method according to claim 1, wherein the dental disorder is dental caries.

22. A method according to claim 1, wherein the dental disorder is tooth sensitivity.

23. A method according to claim 1, wherein the dental hard tissue and pulpal disorders are chosen from dental caries, pain, tooth wear, discoloration, dentine hyper-sensitivity, dental tissue congenital malformations and combinations thereof.

24. The method according to claim 1, wherein said bioactive glass is 45S5.

25. A method of treating a human suffering from a dental disorder, comprising applying a bioactive glass as an air abrasive agent directly to an affected dental surface of the human.

26. A method of treating a human suffering from or susceptible to dental hypersensitivity, comprising applying a bioactive glass as an air abrasive agent directly to an area of said human affected by said dental hypersensitivity.

27. A method of treating a human suffering from or susceptible to dental discoloration, comprising applying a bioactive glass as an air abrasive agent directly to an area of said human affected by said dental discoloration.

* * * * *